(12) United States Patent
Stewart et al.

(10) Patent No.: US 9,883,831 B1
(45) Date of Patent: Feb. 6, 2018

(54) DIGITAL MEDICAL EVALUATION AND TESTING ON A TOUCH SCREEN DEVICE

(71) Applicant: Texas Health Biomedical Advancement Center, Inc., Arlington, TX (US)

(72) Inventors: Robert Malcolm Stewart, Arlington, TX (US); Michael R. Skupien, Arlington, TX (US)

(73) Assignee: Texas Health Biomedical Advancement Center, Inc., Arlington, TX (US)

( * ) Notice: Subject to any disclaimer, the term of this patent is extended or adjusted under 35 U.S.C. 154(b) by 116 days.

(21) Appl. No.: 14/168,652

(22) Filed: Jan. 30, 2014

(51) Int. Cl.
*G09B 19/00* (2006.01)
*A61B 5/00* (2006.01)
*A61B 5/16* (2006.01)

(52) U.S. Cl.
CPC ............ *A61B 5/162* (2013.01); *A61B 5/4088* (2013.01)

(58) Field of Classification Search
CPC .............................. A61B 5/4088; A61B 5/162
See application file for complete search history.

(56) References Cited

U.S. PATENT DOCUMENTS

| | | | |
|---|---|---|---|
| 6,485,417 B1 | 11/2002 | Bowles et al. | |
| 6,517,480 B1 | 2/2003 | Krass | |
| 6,820,037 B2 | 11/2004 | Simon | |
| 6,896,656 B2 | 5/2005 | Krass | |
| 9,122,388 B2 | 9/2015 | Hwang | |
| 9,131,063 B2 | 9/2015 | Larson et al. | |
| 9,152,212 B2 | 10/2015 | Gunn | |
| 9,152,306 B2 | 10/2015 | Anderson et al. | |
| 9,158,372 B2 | 10/2015 | Lombardi et al. | |
| 9,182,903 B2 | 11/2015 | Lombardi et al. | |
| 9,183,655 B2 | 11/2015 | Baker et al. | |
| 9,208,384 B2 | 12/2015 | Conwell et al. | |
| 9,208,692 B2 | 12/2015 | Considine et al. | |
| 2002/0155419 A1* | 10/2002 | Banerjee | G09B 7/00 434/322 |
| 2002/0192624 A1* | 12/2002 | Darby | A61B 5/16 434/236 |
| 2003/0167149 A1* | 9/2003 | Simon | A61B 5/16 702/182 |
| 2004/0167380 A1* | 8/2004 | Simon | A61B 5/16 600/300 |
| 2005/0273017 A1* | 12/2005 | Gordon | A61B 5/048 600/544 |
| 2010/0240016 A1* | 9/2010 | Ween | G06F 19/3487 434/236 |

(Continued)

*Primary Examiner* — Michael C Stout
*Assistant Examiner* — Nicholas E Kolderman
(74) *Attorney, Agent, or Firm* — Gardere Wynne Sewell LLP

(57) ABSTRACT

Cognitive tests are loaded onto myriad touch screen client computing devices. Patients are administered the tests using the touch screen devices, and their performance is captured and transmitted to cloud servers that store the patient information of all the touch screen devices in a database. In addition to cognitive test results, touch screen devices may also transmit patient medical information for storage in the database. Consequently, the database includes a large population of performance and medical data that can be evaluated to gain insights into cognitive disorders and create more effective digital tests for their diagnosis and treatment.

19 Claims, 8 Drawing Sheets

(56) References Cited

U.S. PATENT DOCUMENTS

| | | | |
|---|---|---|---|
| 2011/0236864 A1* | 9/2011 | Ashford | A61B 5/4088 |
| | | | 434/236 |
| 2012/0214143 A1* | 8/2012 | Severson | G06F 19/3431 |
| | | | 434/236 |
| 2012/0238831 A1* | 9/2012 | Benford | A61B 5/162 |
| | | | 600/300 |
| 2013/0209977 A1 | 8/2013 | Lathan et al. | |
| 2014/0066802 A1* | 3/2014 | Kaula | A61B 5/7475 |
| | | | 600/554 |
| 2014/0255900 A1* | 9/2014 | Ferrara | G09B 5/08 |
| | | | 434/362 |

* cited by examiner

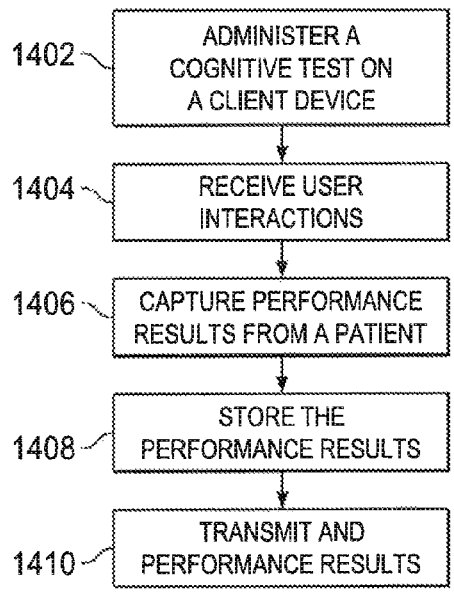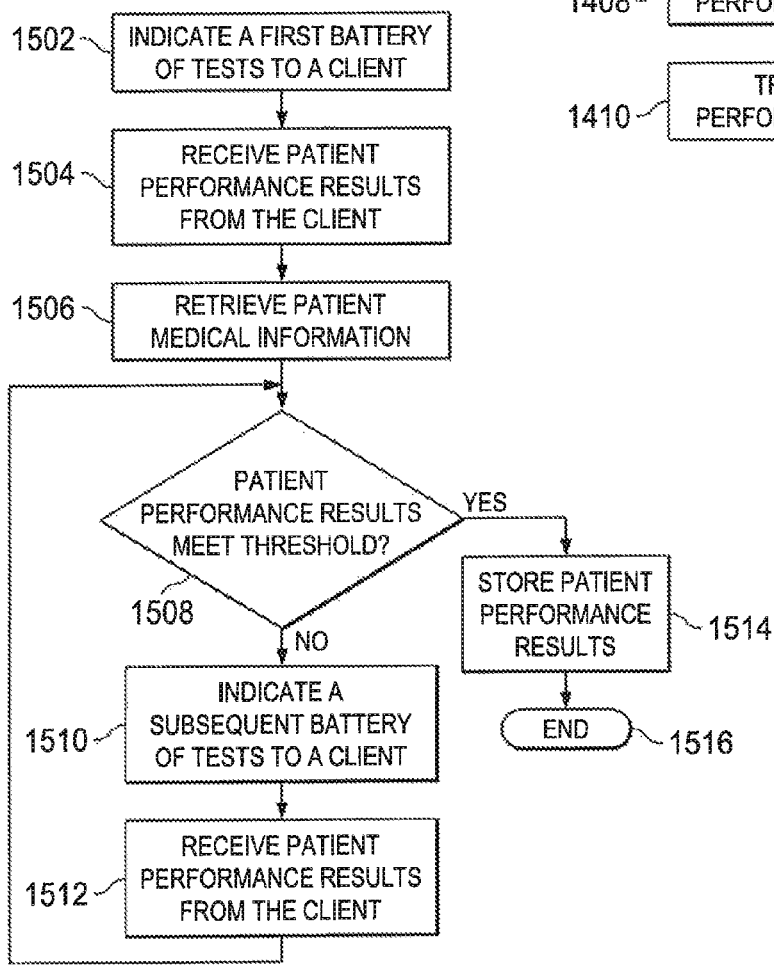

DIGITAL MEDICAL EVALUATION AND TESTING ON A TOUCH SCREEN DEVICE

BACKGROUND

There is a national epidemic of cognitive impairment in the world. In the United States alone, millions of individuals suffer from the most common form of cognitive impairment, Alzheimer's disease. Millions more suffer from some type of dementia, such as Parkinson's disease dementia, Lewy body dementia, fronto-temporal dementia, vascular and stroke dementia, and traumatic brain injury dementia. The number of individuals affected by dementia in the United States alone is expected to swell to 15 million people by 2025, which if true, will have a devastating economic impact of billions of dollars yearly in direct and indirect costs to society. Thus, there is a tremendous need for clinical care and research on cognitive and memory disorders. At any given time, approximately one quarter of all hospital patients aged 65 and older are dealing with Alzheimer's disease or other dementias. These patients typically have more complications than those without a memory disorder, require additional resources, and are more likely to be readmitted to a healthcare facility later.

Recent biomarker studies (neuroimaging with amyloid PET scans or cerebrospinal fluid) indicate that the biological process for Alzheimer's disease starts early in an asymptomatic manner, perhaps even twenty years before symptoms begin. This knowledge has led to a revision in the diagnosis and staging of Alzheimer's disease with the hope that early detection will lead to early treatment and offer a better prognosis. Alzheimer's disease is now divided into an 1) asymptomatic preclinical phase, 2) a symptomatic pre-dementia phase referred to as mild cognitive impairment (MCI), and 3) a dementia phase. The pre-dementia phase is also divided into 3 stages: the first characterized by asymptomatic amyloidosis, the second shows evidence of synaptic dysfunction, and the third has subtle cognitive changes not evident in day-to-day behavior. The Centers for Medicare & Medicaid Services (CMS) has now mandated cognitive screening annual physical examinations to begin detecting the various stages. Moreover, identifying individuals with cognitive impairment without dementia, also known as mild cognitive impairment (MCI), is useful in treating patients at an earlier stage. A significant percentage of the elderly population (65+) are at risk for MCI, and this risk increases as patients age.

Cognitive impairments are not limited to solely the elderly. Concussions and other types of head trauma occur in many areas of life, e.g., accidents, etc. Research is continuing to evolve and reveal how repetitive head trauma can greatly increase a person's chance for acquiring later memory disorders. Even mild repetitive head trauma, such as blows to the head that do not leave a person woozy or seeing stars is showing to be the cause of later memory problems in life. The first step in treating cognitive impairments caused by head trauma is to first diagnose their occurrence.

Traditional cognitive evaluations have not progressed into the digital age. Diagnostic testing is typically conducted on paper with a clinician observing or manually grading the results. For example, a patient may be instructed to trace a line through a maze on a piece of paper while a clinician times the exercise and evaluates how close inside the maze lines the patient draws. Or a clinician may time how fast a patient touches a sequence of colored dots on a piece of paper. Manually administering and scoring tests introduces a level of human error to the testing process.

Modern computer tablets, smart phones, and other computing devices have evolved rapidly over the years, boasting incredibly fast processors, speedy Web connections, ample computer memory, and very precise touch screens. This combination of computing power has led to a proliferation in software applications being designed as all sorts of unique and specialized tools. There have been myriad cognitive enhancement products that address the wellness market. But there is no mobile medical device approved by the Food and Drug Administration (FDA) developed specifically as a medical device for the clinical assessment of MCI, traumatic brain injuries, Alzheimer's disease, and other dementias.

SUMMARY

This summary is provided to introduce a selection of concepts in a simplified form that are further described below in the Detailed Description. This summary is not intended to identify key features or essential features of the claimed subject matter. Nor is this summary intended to be used as an aid in determining the scope of the claimed subject matter.

One aspect of the present invention is directed to providing one or more cognitive tests on a computing device with a touch screen display and measuring patient performance of an administered test. The computing device includes a processor, memory, touch screen display, and possibly a network connection along with other peripherals (e.g., speaker, microphone, mouse, etc.). The cognitive tests may be stored in memory of the computing device or on a remote server and accessed through the network connection. The tests may be administered through display on the touch screen, and patient interaction with the touch screen may be captured and used to assess a patient's neurological state. Patient test performance and medical information may be transferred and stored on a server.

Another aspect of the invention relates to a networked computing architecture allowing clinicians or other test developers to design and upload their own battery of medical tests from one computing device to a centralized server that can transmit the battery of tests to other client computing devices. The clinicians' or developers' tests can be created on a client computing device and uploaded to a server from which other client computing devices can download the battery. This framework provides an expanded framework giving clinicians and developers the freedom to create their own tests to be downloaded and administered on other client devices.

Still another aspect of the invention relates to a backend database that can receive and store patients test results on administered cognitive tests and patient medical information. The results may be stored in a central or relational database, and the results may be mined for statistical patterns correlated between neurological illnesses and common patient test results. The stored test results may be used to better understand neurological illnesses as well as to gauge the efficacy of tests for diagnosing the illnesses.

Still another aspect of the invention relates to administering neurological, or other medical, tests on a touch-screen computing device, using a disparate server to interpret patient interactions with the test, and the server instructing the touch-screen computing device to modify a portion of the test based on the server's interpretation. The touch-screen computing device effectively communicates the patient's performance on the test, and the server stores the patient medical information.

BRIEF DESCRIPTION OF DRAWINGS

Embodiments are illustrated by way of example in the accompanying figures not necessarily drawn to scale, in which like numbers indicate similar parts, and in which:

FIG. 14 illustrates a flowchart of a work flow for administering digital batteries of tests on a client computing device.

FIG. 15 illustrates a flowchart of a work flow for administering digital batteries of tests on a client computing device

DETAILED DESCRIPTION OF THE EMBODIMENTS

Figure 1:
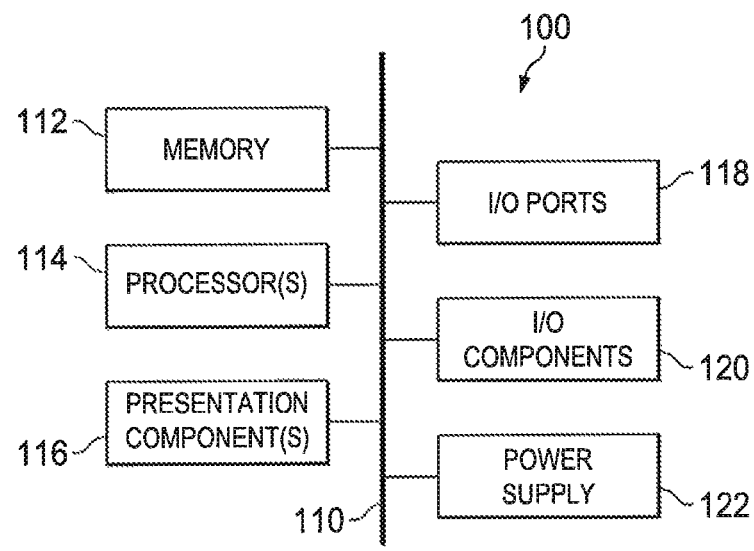
FIG. 1 is a block diagram of an exemplary computing environment suitable for implementing embodiments discussed herein.

The subject matter of embodiments of the present invention is described with specificity herein to meet statutory requirements. But the description itself is not intended to necessarily limit the scope of claims. Instead, the claimed subject matter might be embodied in other ways to include different steps or combinations of steps similar to the ones described in this document, in conjunction with other present or future technologies. Terms should not be interpreted as implying any particular order among or between various steps herein disclosed unless and except when the order of individual steps is explicitly described.

In general, embodiments are directed to a computer-based methodology for assessing patient's cognitive state or capabilities using interactive software applications presented on a touch-screen computing device, e.g., a tablet, smartphone, handheld, laptop, or the like. The software applications present a set of interactive tests on the touch-screen computing device with instructions on how to complete various exercises. The patient's performance is measured, and performance results are transferred to a remote computing server (in one embodiment) for storage with results from other patients. Different neurocognitive abilities may be measured using the interactive tests. For example, the tests may be designed to measure a patient's memory, hand-eye coordination, ability to follow instructions, perceptual ability, attention, cognitive dysfunction, dexterity, and the like. The patient's performance can then be utilized to develop a profile (a red flag) to alert the clinician to the possibility or likelihood of a cognitive decrement or a neurocognitive disorder (e.g., dementia, traumatic brain injury, concussion, mild cognitive impairment, Alzheimer's, and the like). In one embodiment, such a profile will serve the clinician as an adjunctive screening methodology, but clinical judgment and additional information will be needed to make and confirm a specific clinical diagnosis, leaving the final diagnosis of a patient's health at the clinician's discretion.

The server receives cognitive test performance information from numerous client computing devices and stores the performance information in a database. The database may be stored, in one embodiment, across multiple backend servers according to a relational or virtual database storage model, such as cloud computing. The plethora of patient information can be mined to understand correlations between patients' performances and cognitive, or other medical, illnesses. In other words, the performance information stored in the database can be analyzed to understand patterns associated with patients who have been diagnosed with different illnesses. For example, a threshold number and pattern of wrong answers to a cognitive test directing patients to identify the next sequential number in a sequence of numbers can be determined from stored results of patients who have previously taken the test.

The software application may take the form of a downloadable application for a computing tablet such as an IPAD® (developed by APPLE®, Inc.), SURFACE™ (developed by MICROSOFT® Corporation), KINDLE® (developed by AMAZON.COM®), Galaxy Note (developed by SAMSUNG® Electronics, Co.), or the like. Embodiments are not limited to running solely on tablets, however, the software application may be downloaded and run on other types of computing devices, such as a handheld computer, laptop, personal computer, smart phone, gaming console, or the like. Different tests may be administered to the patient on the interactive, touch-screen computing device. Examples include, without limitation, the following.

A "trail making test" measures a patient's motor speed and attention by having the patient draw lines connecting a series of letters and numbers. A "finger tapping test" measures the motor speed and dexterity of a patient being instructed to tap a displayed spot either as fast as possible or at a specific cadence. A picture memory test measures visual and abstraction ability by displaying a set of pictures (individual or grouped) and asking the patient to name the displayed single object (recall) or identify the relationships or class of the grouped object (abstraction). An "orientation test" asks a patient to enter specific information about the present time (e.g., date, time, month, year, etc.) and/or location (e.g., city, state, country, building, etc.). An "attention/flexibility test" presents a series of letters and numbers for specific amount of time and provides multiple options describing the presented letter or number (e.g., whether it was a consonant, vowel, even number, odd number, etc.) for measuring how fast and accurate the patient chooses the correct option.

A "selected attention response (SAR) inhibition test," such as the Eriksen flanker test, assesses a patient's ability to suppress responses that are inappropriate in a particular context. The test presents a target flanked by non-target stimuli corresponding to either the same directional response as the target (congruent flankers), the opposite response (incongruent flankers), or neither (neutral flankers). The patient is then asked to select a descriptive option that corresponds to the target.

A "language test" measures a patient's ability to recall a sequence of words displayed for short amounts of time (e.g., 1-4 seconds), wait a delay period, re-present the sequence of words, and instruct the patient to correctly identify the sequence. A "visual spatial test" presents letters or numbers to the patient along with various distractions and measures how fast, and accurately the patient can tap through a logical sequence of the displayed letters or numbers. A "working memory test" displays a sequence of numbers or letters to the patient who is instructed to repeat the sequence backwards and forwards. A "memory for numbers test" presents a patient with a series of numbers, and requests that the patient enter the series of numbers backward using a key pad. The number will progress through a sequence, and the test continues until the subject makes a mistake. A "memory for words test" presents the subject with a series of randomly chosen words and requests the subject repeat the words after a set delay (e.g., 5 minutes). Then, the patient is given additional series of words that includes the randomly chosen words as well as additional distractors and asked to indicate yes or no as to whether displayed words were in the original series.

In a "verbal fluency test," the subject is asked to name as many animals as possible in a given timeframe (e.g., 1 minute). In a "letter tapping test," a patient is given a series of letters and must tap once for a specific letter (e.g., A), twice for a second letter (e.g., C), and not tap for other letters to test the patient's attention and inhibition.

Different embodiments will use combinations of the aforementioned tests to profile different neurocognitive abilities of a patient, and the resultant profiles of the patients can be either provided to a clinician as an adjunctive resources, used to diagnose the patient, or used in an iterative manner to automatically determine additional testing—through other batteries of tests—are needed. To clarify the latter, some embodiments will present a first battery of tests (e.g., SAR, letter tapping, working memory), and if the patient performs below a certain threshold, a second battery of tests (e.g., visual spatial, language) is subsequently provided to capture additional testing points. In other words, batteries (i.e., groups) of tests can be provided iteratively to patients based on their test performance.

The tests described herein and shown in the accompanying figures are provided merely for explanatory purposes of some particular embodiments, and are not provided as an exhaustive list for limiting all embodiments of the present invention. Some embodiments may include additional tests not mentioned herein.

For the sake of clarity, embodiments discussed herein refer to batteries of neurocognitive tests. The networking environment described in FIG. 2 may also be used to accommodate batteries of testing from other areas of medicine, such as cardiology, orthopedics, rheumatology, pathology, psychiatry, or the like. Tests in these different medical disciplines may be administered from servers to different client computing devices, and patient test performance may be captured by the client computing devices and stored in backend databases. Thus, embodiments are not limited to neurocognitive tests.

Referring to the drawings, FIG. 1 illustrates an example operating environment of a computing device 100 capable of presenting interactive cognitive tests to a patient, according to one embodiment. Computing device 100 is but one example of a suitable computing environment and is not intended to suggest any limitation as to the scope of use or functionality of the invention. Neither should computing device 100 be interpreted as having any dependency or requirement relating to any one or combination of components illustrated. In one embodiment, computing device 100 is a mobile tablet (e.g., an IPAD® from Apple, Inc.®, a SURFACE™ from the Microsoft Corporation®, or the like). In other embodiments, computing device 100 may be a smart phone, gaming console, handheld device, or device capable of executing computer instructions.

Embodiments include computer code or machine-useable instructions, including computer-executable instructions such as program modules, being executed by a computer or other machine, such as a PDA or other handheld device. Generally, program modules including routines, programs, objects, components, data structures, and the like, refer to code that perform particular tasks or implement particular abstract data types. Embodiments described herein may be practiced in a variety of system configurations, including hand-held devices, consumer electronics, general-purpose computers, more specialty computing devices, etc. Such program modules may be initially installed on the computing device 100 or downloaded to the computing device 100 from a centralized repository of software applications. Embodiments described herein may also be practiced in distributed computing environments where tasks are performed by remote-processing devices that are linked through a communications network.

With continued reference to FIG. 1, computing device 100 includes a bus 110 that directly or indirectly couples the following devices: memory 112, one or more processors 114, one or more presentation components 116, input/output ports 118, input/output components 120, and an illustrative power supply 122. Bus 110 represents what may be one or more busses (such as an address bus, data bus, or combination thereof). Although the various blocks of FIG. 1 are shown with lines for the sake of clarity, in reality, delineating various components is not so clear, and metaphorically, the lines would more accurately be grey and fuzzy. For example, one may consider a presentation component such as a display device to be an I/O component. Also, processors have memory. It will be understood by those skilled in the art that such is the nature of the art, and, as previously mentioned, the diagram of FIG. 1 is merely illustrative of an exemplary computing device that can be used in connection with one or more embodiments of the present invention. Distinction is not made between such categories as "mobile tablet," "handheld device," "laptop," "robotic kiosk," "gaming console," or the like, as all are contemplated within the scope of computing device 100.

Computing device 100 typically includes a variety of computer-readable media. By way of example, and not limitation, computer-readable media may comprise Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices.

Memory 112 includes computer-storage media in the form of volatile and/or nonvolatile memory. For purposes of this disclosure, computer-storage media, and thus memory 112, does not include propagating signals or other carrier waves. Memory 112 may be removable, nonremovable, or a combination thereof. Exemplary hardware devices include solid-state memory, hard drives, cache, optical-disc drives, etc. Computing device 100 includes one or more processors that read data from various entities such as memory 112 or I/O components 120. Presentation component(s) 116 present data (text, images, audio, video) indications to a user or other device and include a touch-screen display for receiving the patient's input in response to the test. The touch screen display may be an infrared (IR), capacitive, resistive, surface acoustic, or similar type of touch screen capable of detecting patient finger or stylus touches. Presentation components 116 may also include a display device, speaker, printing component, vibrating component, etc.

Within memory 112, computing device 100 may store the one or more software applications that, when executed, present different neurocognitive tests for testing a patient's cognitive abilities. When executed, the tests are presented on presentation component 116, and may time how long it takes the patient to complete a test or a portion of the test. Additionally, the tests may also monitor how well the patient performs a specific task by comparing the patient's interactions with graphics being presented on presentation component 116. Touches may be captured on a touch screen. Audio may be captured through a microphone. Images may be captured through a camera. Identifying features may be captured through different scanners on the device (fingerprint, palm print, iris, etc.). The orientation of computing device 100 through accelerometer may be captured. Additionally, software on the computing device 100 may be configured to recognize facial structures, eye locations, and gestures of a patient. Additional concurrent simultaneous affective/autonomic information, such as pulse, temperature, sweating, brain waves (e.g., through an electroencephalography or "EEG"), or the like, may be input through peripheral devices of the computing device 100. This adjunctive information would parallel the cognitive information to more clearly define the overall cognitive, emotional, and attentional state at the time of the examination.

I/O ports 118 allow computing device 100 to be logically coupled to other devices including I/O components 120, some of which may be built in. Not only may the tests measure patient touches on a touch screen, but the tests may also incorporate other peripheral devices that communicate with or through I/O ports 118. Examples of peripherals include, without limitation, microphones, speakers, headset, headphones, accelerometers, joysticks, mice, touch pads, cameras (e.g., standard, video, stereo, depth-aware, etc.), global positioning system (GPS) chips, scanners, or other typical peripherals.

Figure 2:
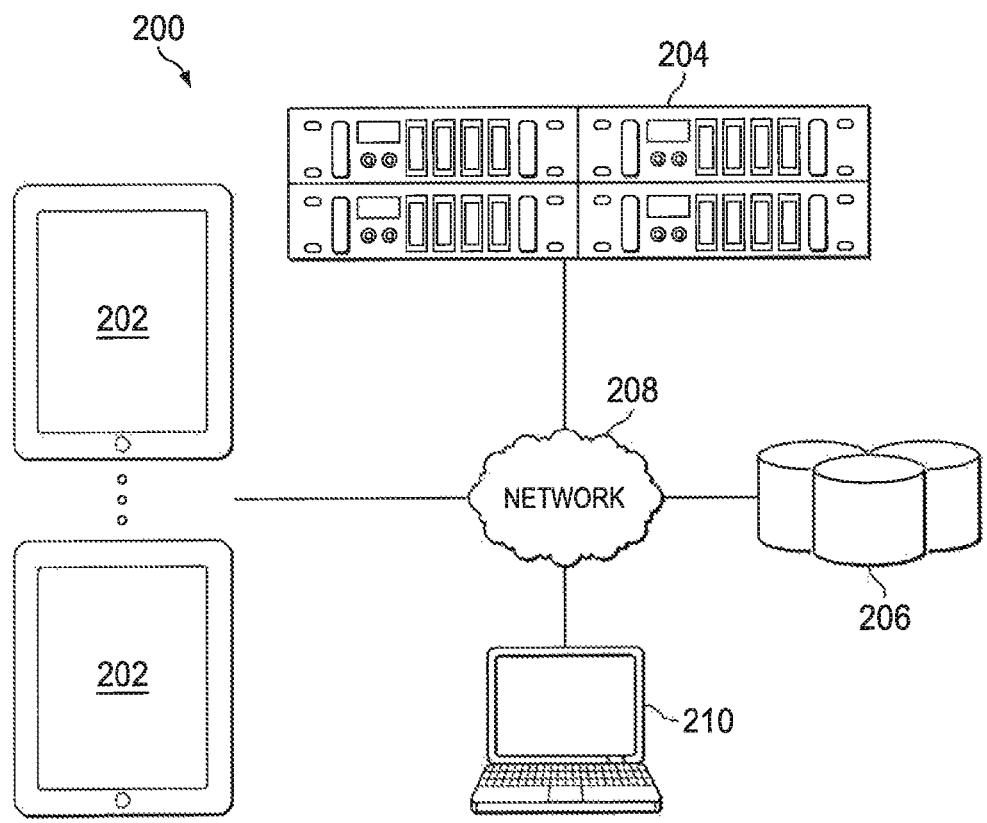
FIG. 2 illustrates a networked environment in accordance with one embodiment.
Figure 3:
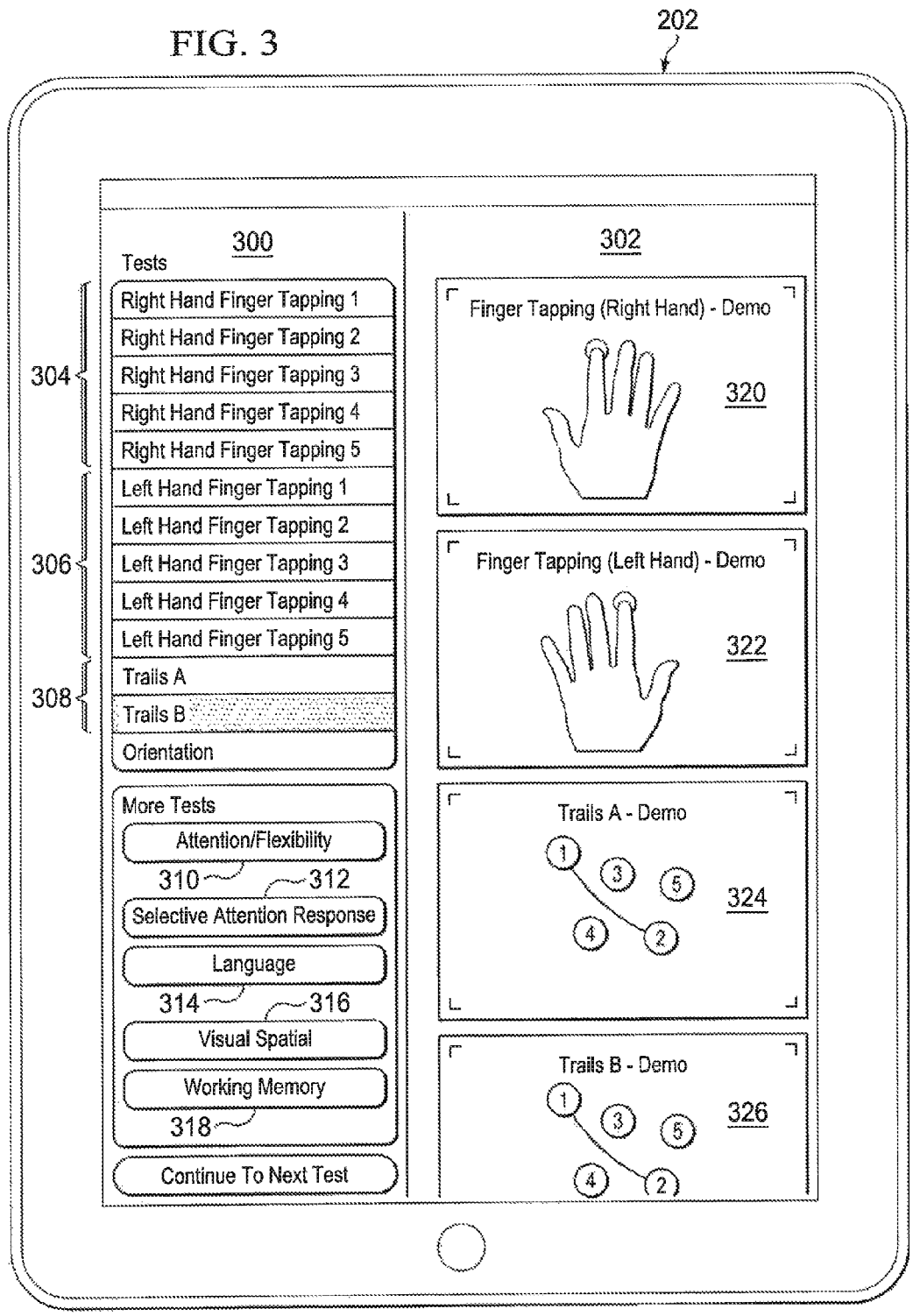
FIG. 3 illustrates a user interface (UI) with menus for selecting a battery of tests on a client computing device.

FIG. 2 illustrates a networking environment 200 in accordance with one embodiment. Networking environment 200 comprises client computing devices 202, servers 204, database cluster 206, and developer computer 210 communicating across a network 208. While client computing devices 202 and developer computing device 210 can take the form of any of the aforesaid computing devices 100, one specific embodiment involves client computing device 202 being a mobile computing tablet (e.g., IPAD®, SURFACE™, etc.) and developer computing device 210 being a laptop or other personal computer (PC).

Network 208 may include any computer network or combination thereof. Examples of computer networks configurable to operate as network 208 include, without limitation, a wireless network, landline, cable line, fiber-optic line, local area network (LAN), wide area network (WAN), or the like. Network 208 is not limited, however, to connections coupling separate computer units. Rather, network 208 may also comprise subsystems that transfer data between servers or computing devices. For example, network 208 may also include a point-to-point connection, the Internet, an Ethernet, a backplane bus, an electrical bus, a neural network, or other internal system.

A test developer uses developer computer 210 to design a cognitive test, or a battery of tests, for client computing devices 202 and upload the tests to server 204, or some other hosting computing device, to make the test available over network 208. Users can then download and run the tests on client computing devices 202. Alternatively, the tests may be preloaded on the client computing devices 202. Once saved, client computing devices 202 can present the developer's test (or battery of tests) to patients, capture patient's test results, and transmit the test results to server 204, which stores the test results in database cluster 206. Test results may alternatively be transmitted directly to database cluster 206 from client computing devices 202, alleviating the need for server 204 to operate as a middle-tier device. The test results are evaluated to measure cognitive traits of the patient, such as the patient's categorical judgment; decision-making, motor command; simple visual forms, edges, and corners; intermediate visual forms and groups; high-level objects; memory; hand-eye coordination; ability to follow instructions; perception; attention; and dexterity. Based on the test results forming the user's profile, a diagnosis or recommendation is given by the clinician responsible for administering the test to either the patient on the client computing device 202 or to a clinician on a separate computing device that indicates whether the patient needs further testing or has a profile consistent with cognitive impairment.

Client computing devices 202 may capture, store, and transmit several different attributes as test results. Touches on a touch screen and the accuracy of such touches to displayed graphics may be captured. The speed in which a patient performs a test or certain tasks in a test may be captured. The accuracy of entered responses may be determined, e.g., whether the patient typed in a given sequence of words in the manner instructed. Biometrics of the patient may be captured during a test, e.g., retinal scan, eye recognition, facial recognition, fingerprint scan, voice recognition, gesture recognition, etc. Patient inputs through a keyboard, microphone, mouse, or other peripheral may be captured. The above are not meant to be an exhaustive list, but are instead provided purely as examples of different data that can be captured and transmitted from client computing devices 202.

In addition to cognitive test results, other type of patient data may be transmitted from computing devices 202 to server 204 and stored in database cluster 206. This information may include wallet-type information (e.g., age, sex, height, weight, race, location, date of etc.); patient medical history; familial medical history (e.g., medical history of parents, grandparents, siblings, etc.); medications; genetics; diagnoses; lab results; pet scans and other types of imaging; profession; police reports; traumatic event details; and other medical, personal, or professional data that is typically captured by healthcare professionals. Collectively, this is information is referred to herein as "patient medical information," and it may be entered manually on client computing devices 202, associated with specific test results by server 204, pulled from a user profile or electronic medical records (EMR) in database cluster 206, or otherwise obtained by a clinician and entered into the database cluster 206 using a separate computing device (not shown).

Server 204 can be used to mine stored serial cognitive test results and patient medical information to analyze the course (amount and direction of change) whether a particular patient has a significant change in profile to suggest improved cognitive function or whether the patient is regressing. For example, server 204 may compare a patient's performance on the SAR inhibition test with results from the same administered test months before.

Also, server 204 may be used to mine stored cognitive test results and patient medical information for certain population of patients or for all patients to test whether specific electronic tests are accurately diagnosing or indicating cognitive impairment in patients. Server 204 may also be configured to monitor the number of times a specific cognitive test is administered, analyze the saved results of the administered test, and determine the number of times the patient results correlate with a clinician's diagnosis of some type of cognitive impairment. In this way, server 204 provides the ability to test the efficacy of different tests for properly identifying patients with particular cognitive impairments. For example, if 95% (or some other percentage) of patients testing positive for a particular cognitive impairment by performing poorly on the visual spatial test correlate are also diagnosed by a clinician to have that cognitive impairment, the test itself can be assumed to be an accurate screener for the cognitive impairment. Moreover, different correlations can be drawn from test results and specific patient medical history similarities—e.g., biomarkers, genetics, family history, medication history, etc.

Database cluster 206 receives and stores test results and medical information from many different patients using client computing devices 202 in a database that may span one or more servers. Storing the test results in the database enables medical researchers to query the database and analyze the test results of many different patients. Such analysis is particularly useful in determining cognitive impairments, treatment options, and tendencies of patients suffering from different illnesses, as well as in evaluating the effectiveness of cognitive tests. For example, a medical researcher may wish to discover the most effective way to treat patients diagnosed as having multiple concussions. To this end, the researcher can query the database in database cluster 206 to understand the patients with multiple concussions historical performance on the Acute Concussion Evaluation (ACE) test administered over computing devices 202. By looking at results from many different patients with multiple concussions, the medical researcher can check how efficiently an administered test indicates a person has a concussion.

Test results may also be used to understand the effectiveness of tests, or batteries of tests, being administered. Tests results stored in database cluster 202 may be queried, either by an administrator or periodically, to understand how well patients who have been diagnosed with a particular neurological illness performed. For example, if 90% of patients eventually diagnosed with concussions performed in a certain way (e.g., selected the wrong sequence of numbers, traced outside of lines on a maze, could not finish answering questions in a certain timeframe, etc.), analytical software may determine that future patients performing similarly likely suffer from a concussion, thus indicating the test properly evaluates patients for concussions.

Client computing device 202 is equipped to capture numerous test metrics as test results. These test metrics include the patient's performance (i.e., whether the patient traced the correct path through maze, correctly indicated a shown letter was a vowel, etc.) and also test metrics measuring the speed and accuracy of the patient's test completion. Examples of test metrics include, without limitation, the speed of touches, accuracy of patient touches on a touch screen, rhythm of touches, touch count, number of correct answers, number of incorrect answers, gestures, gaze speed, and any other metric that can be captured by the client computing device 202.

In one embodiment, server 204 evaluates test results on batteries of tests based on the evaluated patient performance and suggests additional batteries of tests for the patient to either a clinician or directly to the client computing device 202. For example, a patient's test results on a first battery of ten tests may be below a certain threshold, prompting the server 204 to signal that the patient should be tested with a second battery of tests or should retake a certain number of the of the original ten tests. In this vein, the server 204 evaluates the patient's performance on a battery of tests and suggests a second round to tests to gain additional perspective about the patient's neurocognitive capabilities. This process may be applied iteratively—i.e., through many rounds of batteries of tests—to gain such a perspective.

When evaluating the patient's performance, the server 204 may be configured to account for different presuppositions based on the patient's medical information, such as gender, age, medical history, genetics, or any of the aforementioned medical information. Server 204 may use such presuppositions to tailor batteries of tests to provide to the user, i.e., by adding or removing certain tests from the battery in different iterations provided to the patient or suggested to a clinician to be provided to the patient. Server 204 is configured to consider test metrics and the presuppositions to make determinations about the patient that are subsequently transmitted to a clinician via a clinician computing device or a Web-hosted cloud computing service. For instance, the server 204 may determine that the patient has a particular (strong, medium, low) likelihood of a specific disorder or may determine that further testing is needed on the patient because she shows signs of a disorder, and the second iteration of testing may include a battery of tests specifically selected by the server 204 to account for presuppositions based on the patient's medical information. Such determinations from the server 204 can be used to diagnose patients, recommend additional testing, or provide an adjunctive data point for a clinician to consider in treating the patient.

Test batteries may include tests from different "test domains," which refer herein to different locations of a patient's body (for neurocognitive) or other parts for different medical tests. For example, a battery of neurocognitive tests may include tests for executive function, visual/spatial function, verbal function, memory, right brain, left brain, specific brain lobes, or other specific brain locations. The same can be performed for other medical fields, e.g., different heart valves for cardiology.

In one embodiment, patient medical information and/or test performance is not stored on the client computing device 202 but is transmitted in an encrypted manner to server 204 to help the manufacturer of the client computing device 202 better promote Internet security and comply with Health Insurance Portability and Accountability Act (HIPPA) requirements.

FIGS. 3-7 illustrate UIs on a client computing device 202 in accordance with different embodiments. Looking initially at FIG. 3, client computing device 202 is shown displaying a UI with a menu portion 300 and a test portion 302. Menu portion 300 presents multiple cognitive tests, shown in the illustrated embodiment as right hand finger tapping tests 304, left hand finger tapping tests 306, trail tests A and B 308, an orientation test, attention/flexibility test 310, selective attention response test 312, language test 314, visual spatial test 316, and working memory test 318. The test portion 302 lists iconic views of the various tests in the menu portion 300 that can be selected and to instruct the running of any of the particular tests 304-318. For instance, icon 320 can be touched—or otherwise selected (e.g., using a mouse pointer)—to initiate a right hand finger tapping test. Similarly, icons 322, 324, and 326 can be selected to respectively indicate a left hand finger tapping test, a first trail test, and a second trail test. Additional or alternative tests, such as those described herein, may be displayed in the menu portion 300 and the test portion 302.

Figure 4:
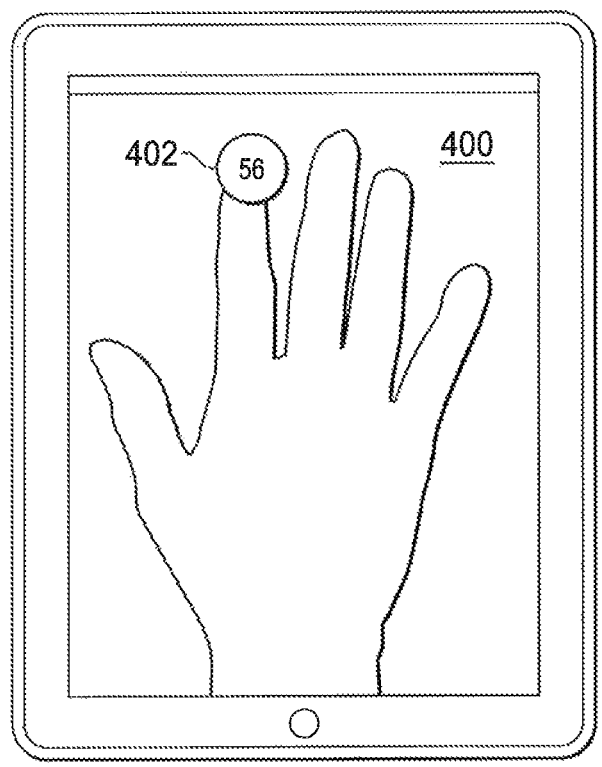
FIG. 4 illustrates a UI for a finger tapping test presented on a client computing device.

FIG. 4 illustrates a UI 400 for a finger tapping test presented on a client computing device 202. The finger tapping test instructs a patient to touch their finger at a tap point 402 on the touch screen of the client computing device 202. In one embodiment, finger tapping test records the number of times the patient touches inside the tap point 402, and may increment a counter displayed to the user, which is shown in the illustrated embodiment as count value "56." The finger tapping test may be timed to see how many taps the patient can register in a given timeframe—e.g., how many touches inside tap point 402 the patient registers within one minute. Additionally or alternatively, the finger tapping test may also count the number of registered touches outside of the tap point 402, monitor the accuracy of taps inside the tap point 402, capture the rhythms of the taps, or detect other test metrics during an administered test. The finger tapping test also, in some embodiments, counts how fast the patient touches the tap point 402 as well as the spatial and temporal pattern of the tapping. For example, a concussed individual may touch the tap point 402 at a much slower rate than a normal patient, or an elderly patient may touch slower than a younger patient. A Parkinson patient might have a different spatial or temporal tapping profile.

Tap point 402 may be kept stationary throughout the finger tapping test or may move throughout UI 400. In one embodiment, tap point 402 moves after a touch is detected, regardless of whether it is inside or outside tap point 402. In another embodiment, tap point 402 moves only after a touch is detected inside tap point 402. In still another embodiment, tap point 402 moves periodically (e.g., after a few seconds). The finger tapping test may capture locations (x/y, coordinates, etc.) on the screen the patient touches inside the tap point 402 and locations on the screen the patient does not touch inside the tap point 402. The responses might be relevant to evaluate location memory and attention.

Touches, counter values, speed, rhythm, and screen location of touches may all be captured by client computing device 202, transmitted to server 204, and stored in database cluster 206. Once stored, these test metrics provide minable data points for diagnosing patients based on test performance and for evaluating the efficacy and accuracy of a finger tapping test presented being administered. In addition to patient performance information, embodiments may also transmit specifics about the finger tapping test being administered, such as the size, shape, color, position, or other particulars of the tap point 402. For example, circular tap points 402 that are only one quarter inch in diameter may present an inordinate amount of false positives for cognitive impairments from large male patients due to larger hand sizes of the patients. To correct for physical attributes of the patients, the tap point 402 may be configured differently for different patients to take physical limitations into account, such as patient size (e.g., height, weight, etc.), hand size, eye sight (e.g., color blindedness, near-sighted, far-sighted, dominant eye, etc.), dominant hand (right handed, left-handed, ambidexterity), and other physical characteristics.

Figure 5:
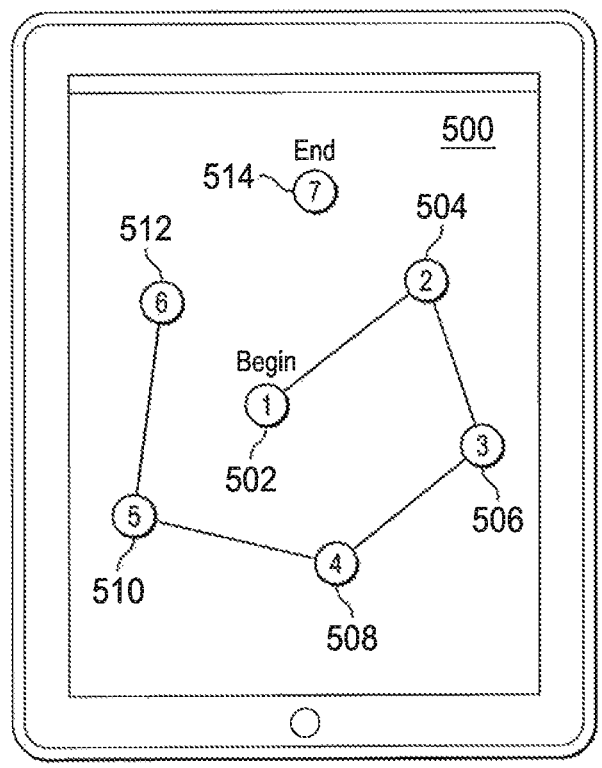
FIGS. 5-6 illustrate UIs for trail tests presented on a client computing device.

FIG. 5 illustrates a UI 500 for a trail test presented on a client computing device 202. The trail test instructs a user to trace their finger from beginning point 502 to ending point 514 though a sequence of intermediary points 504-512 according to a sequence defined by indicators in the points themselves. The shown indicators comprise a sequence of numbers, but other embodiments may use different indicators.

Figure 6:
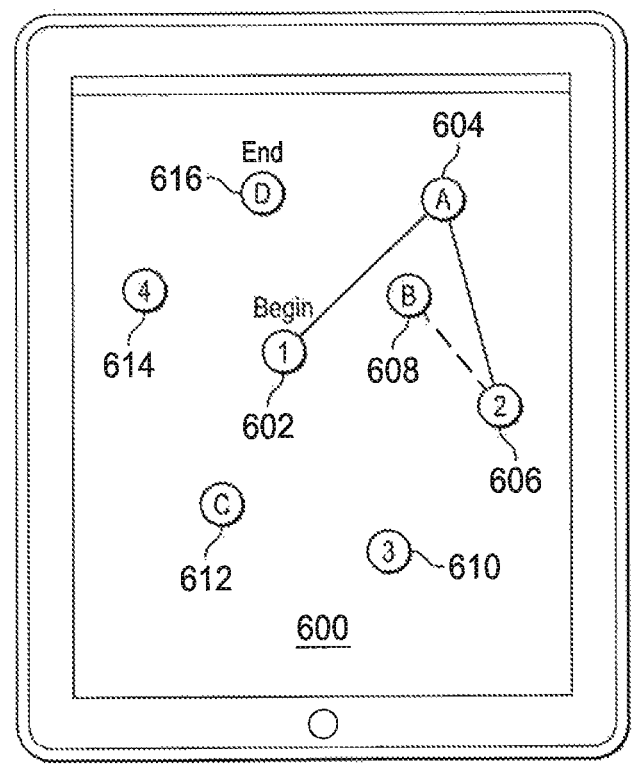

FIG. 6 illustrates a UI 600 that uses a mixture of numbers and letters as trail indicators to instruct a patient on tracing from beginning point 602 to ending point 616, whereby the user is to trace from number to letter as they trace in a progressive manner (e.g., 1, A, 2, B, 3, C, and so on) until they reach the ending point 616. Other indicators besides letters or numbers may be used, such as images, arrows, or animations, or the like.

Figure 7:
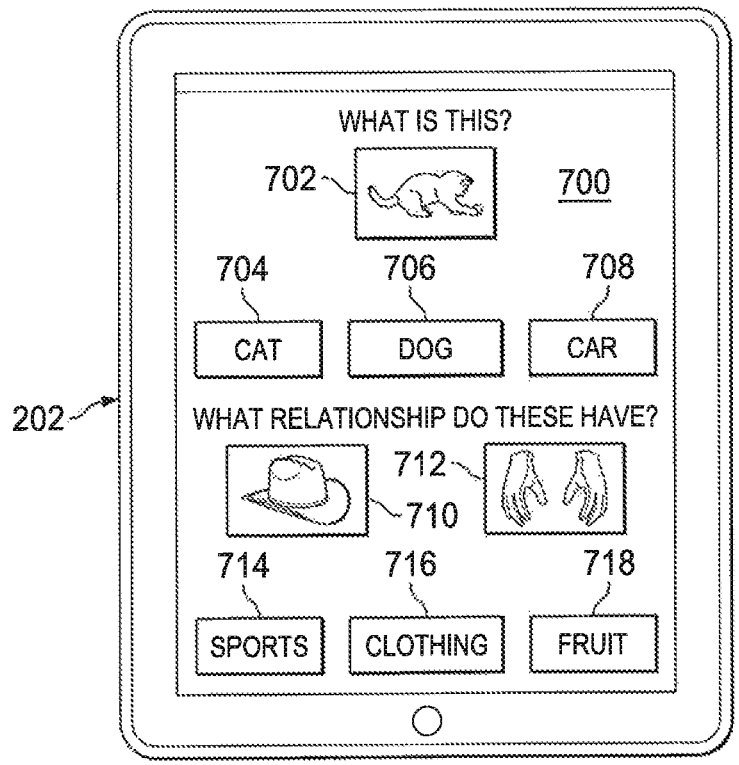
FIG. 7 illustrates a UI presenting a visual memory test on a client computing device.

FIG. 7 illustrates a UI 700 presenting a visual memory test on a client computing device 202. The memory test involves to UI portions. In the upper portion, a single image 702 is shown and the patient is asked to select which of the descriptive options 704-708 accurately describes the image 702. In the lower portion, multiple images 710 and 712 are shown and the patient is asked to select a relationship, similarity, or different of the two from the relationship options 714-718. Correctness and the speed of the patient's selection may be captured by client computing device 202 and transmitted to the server 204. In the shown embodiment, options 704 and 716 are the correct options.

In another embodiment, the patient is given a series of ten pictures at two second intervals, a delay is given, and then the patient is shown a second sequence of pictures that include some of the originals and some distractor pictures. The patient is then be asked to indicate whether each shown image was originally shown or not.

Figure 8:
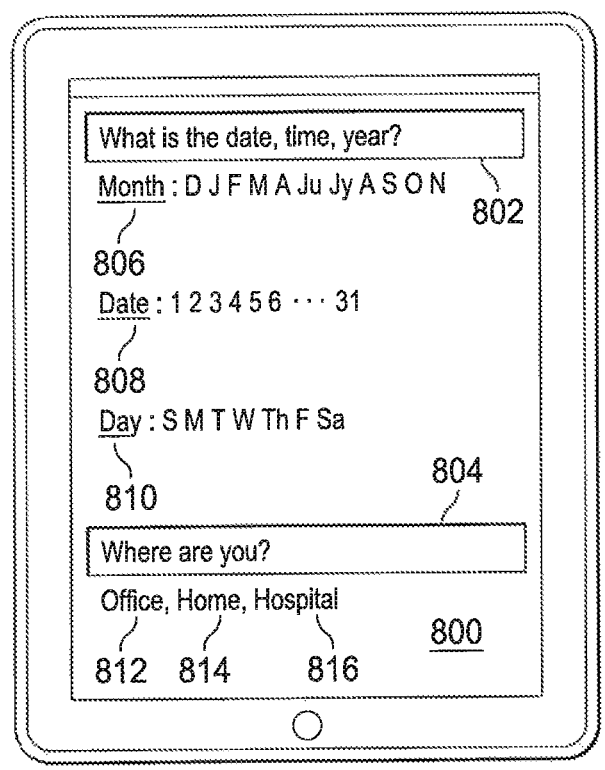
FIG. 8 illustrates a UI presenting an orientation test on a client computing device.

FIG. 8 illustrates a UI 800 presenting an orientation test on a client computing device 202. The orientation test provides asks a patient to enter specific information about the present time (e.g., date, time, month, year, etc.) and/or location (e.g., city, state, country, building, etc.) in UI 800. Question portions 802 and 804 respectively ask the patient to select the present date/time/year and location. The twelve months of the year are displayed in portion 806 in an interactive format whereby the patient can select the appropriate month. The date and day are similarly presented in interactive portions 808 and 810 for selection, as are selectable options 812-816 for the present location of the patient. The patient's completion of the orientation test is timed and results are analyzed—either by the client computing device 202 or the server 204—to evaluate the patient's performance.

Figure 9:
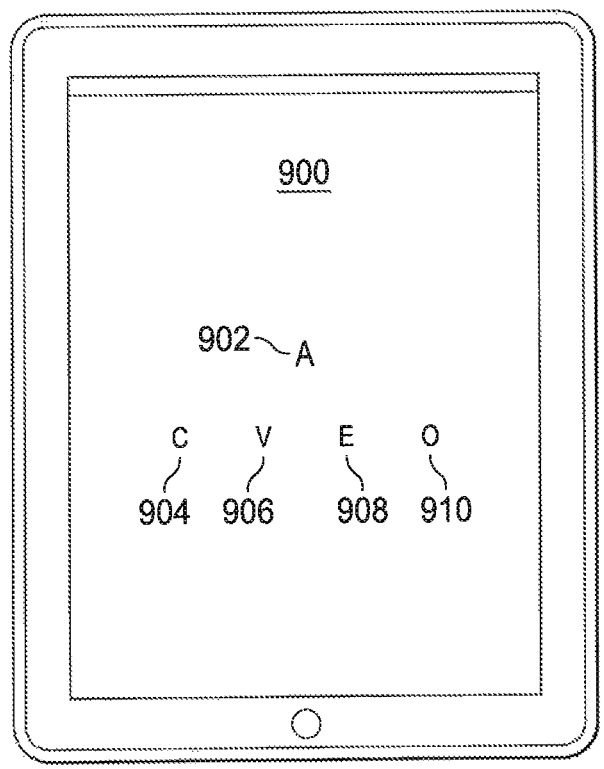
FIG. 9 illustrates a UI presenting an attention/flexibility test on a client computing device.

FIG. 9 illustrates a UI 900 presenting an attention/flexibility test on a client computing device 202. The attention/flexibility test presents a series of letters or numbers at location 902 for a specific amount of time and provides multiple interactive options 904-910 for describing the presented letter or number. In the shown embodiment, the patient is being asked whether the shown letter is a consonant (C 904), vowel (V 906), even number (E 908), odd number (O 910). Once the patient enters a response by touching one of the options 904-910, the next letter or number is presented at location 902, and the patient is asked to select the appropriate option 904-910. Other options may be used, such as, without limitation, upper/lower case, prime/non-prime number, divisible by a certain number (e.g., 3, 4, 5, and the like), etc., and while some embodiments will keep the options 904-910 static during the test, others will dynamically change options 904-910 as the letter/number at location 902 changes.

The patient's completion of the attention/flexibility test is timed and results are analyzed—either by the client computing device 202 or the server 204—to evaluate the patient's performance. This is an attention test, and use of both numbers and letters provides an avenue for testing the left and right hemispheres of the patient's brain: the right hemisphere has shown to be responsible for handling numbers, and the left hemisphere has shown to be responsible for handling language and letters.

Figure 10:
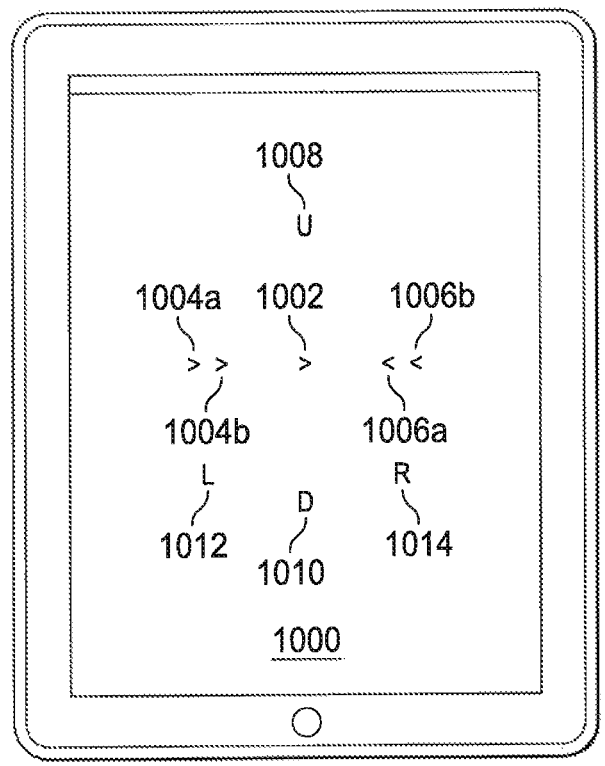
FIG. 10 illustrates a UI presenting a SAR test with an inhibition component on a client computing device.

FIG. 10 illustrates a UI 1000 presenting a SAR test with an inhibition component on a client computing device 202. The SAR inhibition test, such as the Eriksen flanker test, assesses a patient's ability to suppress responses that are inappropriate in a particular context. This test presents a target 1002 flanked by non-target stimuli 1004*a*-*b* and 1006*a*-*b* corresponding to either the same directional response as the target 1002 (i.e., congruent flankers), the opposite response (i.e., incongruent flankers), or neither (i.e., neutral flankers). The patient is then asked to select from interactive options 1008-1014 that correctly describe the target 1002. The interactive options include different directions: up (U 1008), down (D 1010), left (L 1012), and right (R 1014). In the shown example, target 1002 is pointing to the right, so the appropriate response is R 1014. The patient's completion of the SAR inhibition test is timed and results are analyzed—either by the client computing device 202 or the server 204—to evaluate the patient's performance. This test can be done with and without the flankers to test the effect of distraction.

Figure 11:
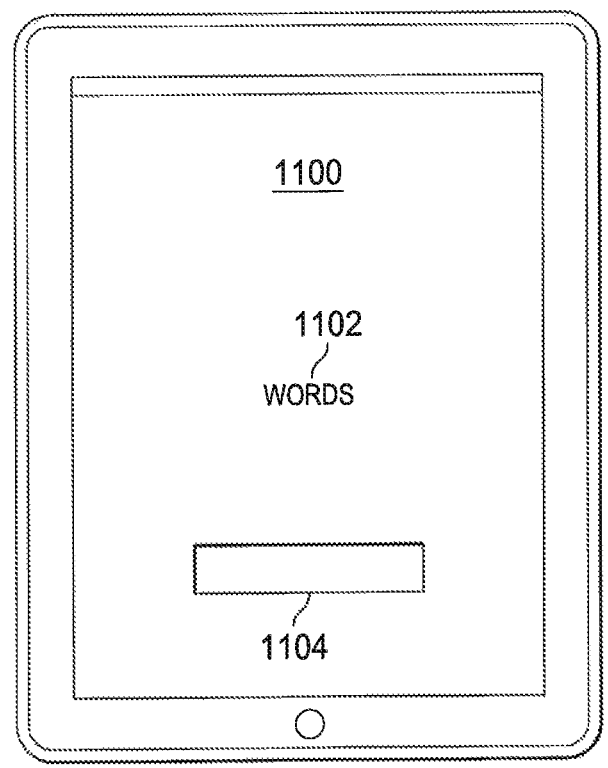
FIG. 11 illustrates a UI presenting a language test on a client computing device.

FIG. 11 illustrates a UI 1100 presenting a language test on a client computing device 202. The language test measures a patient's ability to recall a sequence of words that are displayed at location 1102 for short amounts of time (e.g., 1-4 seconds). In one embodiment, 10 words are each displayed for a set amount of time (e.g., 2 seconds) in a sequence, and a delay is provided during which nothing or distractors are displayed, and then the initial sequence of words are displayed again. The words may be displayed for a set amount of time or until a user touches the word, or some other indication (e.g., an arrow). After the word sequence is presented (either once or multiple times) a delay of 5 minutes occurs. The patient is then first asked to recall from memory and to enter the previously presented words in text box 1104. In the second recognition part of the test, 10 additional randomly selected words (distractors) like "baseball," "iron," and "horse" may be flashed at location 1102 and intermixed with the original 10 displayed words. The patient must then indicate yes or no if the word has been presented before. Words may be presented in shorter or longer timeframes, as may the delays. The patient's completion of the language test is timed and results are analyzed—either by the client computing device 202 or the server 204—to evaluate the patient's performance.

Figure 12:
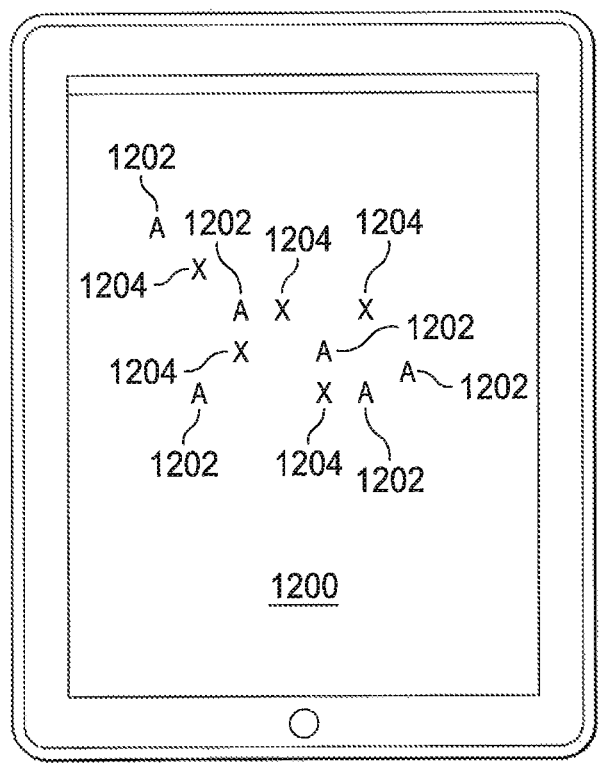
FIG. 12 illustrates a UI presenting a visual spatial test on a client computing device.

FIG. 12 illustrates a UI 1200 presenting a visual spatial test on a client computing device 202. In one embodiment, a letter 1202 (large capitals, small capitals, or a combination) is randomly displayed in the four quadrants of a display panel, and additional distractor letters 1204 are also randomly displayed. The patient is instructed to tap all the same non-distractor letters 1202 regardless of size to test the patient's visual attention. Tapping distractor letters 1204 is recorded as an error.

In another embodiment, the visual spatial test measures how fast and accurately the patient can tap through a logical sequence of the displayed letters or numbers. For example, letters may progress forward or backward alphabetically, numbers may progress forward or backward in numerical order, words may progress through a sentence, or the like. Once the patient touches a letter 1202 or distractor letter 1204, a new UI screen is shown with the next sequential letter 1202 surrounded by distractors 1204. The goal in this embodiment is for the patient to progress through the sequence with minimal number of touches of the distractors 1240. The patient's completion of the visual spatial test is timed and results are analyzed—either by the client computing device 202 or the server 204—to evaluate the patient's performance.

Figure 13:
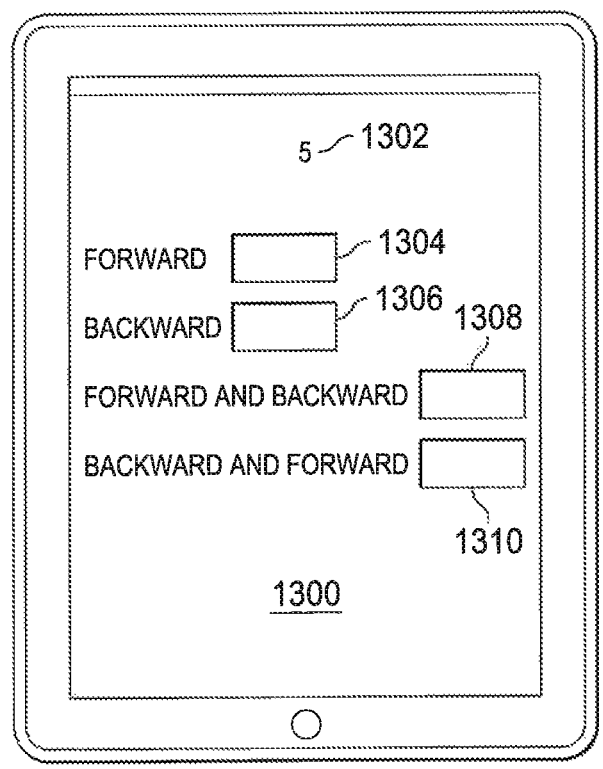
FIG. 13 illustrates a UI presenting a memory test on a client computing device.

FIG. 13 illustrates a UI 1300 presenting a memory test on a client computing device 202. The memory test presents a patient with a series of numbers at location 1302 and instructs the patient to enter the series of numbers in different sequences, such as forward (e.g., starting with five numbers), backward (e.g., starting with three numbers), forward and backward, and backward and forward in text fields 1304, 1306, 1308, and 1310, respectively. The sequence of numbers will progress through a sequence, and the test continues until the patient makes a mistake. In one embodiment, if a patient is unable to complete the sequence at a certain level, the sequence is shortened by one or more integers and the test repeated. Letters may alternatively be displayed, as may a combination of letters and numbers. The sequence may be displayed repetitively with a delay (e.g., 1-10 minutes) or distractors between presentations. The patient's completion of the memory test is timed and results are analyzed—either by the client computing device 202 or the server 204—to evaluate the patient's performance.

The previously discussed tests illustrated in FIGS. 2-13 are merely examples and are not meant to limit all embodiments. The performance tests results from such tests may be used either alone or in conjunction with other patient information and medical records to indicate whether a patient either has or likely has a cognitive impairment, such as a dementia, Alzheimer's disease, traumatic brain injury, or other cognitive issues. Such information may also be used in the treatment of patients with cognitive impairments, to monitor their progress, or to evaluate the efficacy of the tests themselves.

FIG. 14 illustrates a flowchart of work flow 1400 for administering digital batteries of tests on a client computing device 202. Initially, the cognitive test, being stored on the client computing device 202 or accessible in the cloud in alternative embodiments, is administered to a patient by being presented and/or displayed on a touch screen client computing device 202 (step 1402). Any of the aforementioned tests may be administered to the patient, and as shown at steps 1404-1410, the patient's responsive interactions to the administered test is received on the client computing device 202, captured, stored, and transmitted to a server 204 or database cluster 206. The receiving server can then store it with other patients' performance results and optionally associate the results with patient medical information. Together, the patient medical information and stored performance results of the cognitive test are added similar data from other patients to create a large population of information that can be mined and analyzed to learn from patients with cognitive impairments and evaluate the effectiveness of cognitive tests (or batteries of tests) for diagnosing or treating cognitive disorders.

FIG. 15 illustrates a flowchart of work flow 1500 for administering multiple batteries of tests on a client computing device 202. In one embodiment, server 204 transmits an indication of a first battery of tests for client computing device 202 to administer to a patient, as shown as 1502. Other embodiments may not receive such an indication from server 204, and may instead just start by administering the initial battery of tests on the client computing device 202 without any indication from the server 204. Once tests are completed, either individually or after the entire battery, client computing device 202 transmits the patient's performance results on the tests to server 204, which receives the test performance results and also retrieves medical information of the patient, as shown as 1504 and 1506. These steps may be performed in parallel or in sequence.

The server 204 determines whether the received performance results meet a certain predetermined threshold, as shown at decision block 1508. The threshold may be based on test performance (e.g., number of correct answers) and/or test metrics (e.g., speed, accuracy, rhythm, etc.), and it may account for different presuppositions based on the patient's medical information (e.g., demographics, genetics, medications, etc.). For example, ten tests in the first battery may need to be completed within a certain time period (test metric) and no more than a specific number of incorrect answers (test result) may be registered for a patient who has diabetes (presupposition based on medical information).

If the patient meets the threshold, her performance results from the battery are stored and administration program is ended, as shown at 1514 and 1516. But if the patient fails to meet the threshold, server 204 makes a determination that additional testing is needed and selects a subsequent battery of tests based to administer to the patient. The tests in the subsequent battery are selected, in one embodiment, based on the performance results from the first battery or are predetermined, in another embodiment. When based on the performance results, the server 204 may be configured to select tests for the second battery based on problem areas indicated in performance results. For example, if the patient showed poor visual/spatial performance, additional visual/spatial tests may be selected for inclusion in the subsequent battery. Tests may also be selected for the subsequent battery based on severity or intensity of the tests. For example, if the patient performed poorly on a verbal test, an easier verbal test may be selected for the subsequent battery. When tests for the subsequent battery are selected, server 204 either transmits the selected tests or otherwise indicates to the client computing device 202 what tests to administer in the subsequent battery, as indicated at 1510. The patient's performance results on these subsequent tests are then captured by the client computing device 202 are transmitted back to the server 204, as shown at 1512. Additionally, tests may also be selected for the subsequent battery based on the performance of other patients with correlating presuppositions or to test specific test cognitive domains (e.g., executive function) that appear to problematic based on the patient's test performance results.

This process of selecting subsequent batteries may be applied iteratively so in many subsequent batteries of tests. The clinician may be included in this process by cutting off the recommendations for subsequent testing or initiating the next phase of testing.

It should be appreciated that the various embodiments disclosed herein are exemplary. Accordingly, various modifications to these embodiments may be made without departing from the scope of the present disclosure and the claims provided below. The claimed subject matter might also be embodied in other ways, to include different steps or combinations of steps similar to the ones described herein, in conjunction with other present or future technologies.

What is claimed is:

1. A computer-implemented method for administering one or more cognitive tests for evaluating a patient for a cognitive impairment, the method comprising:
    displaying, at a touch screen computing device having a user interface, a first digital cognitive test for testing one or more cognitive functions of the patient, the first digital cognitive test being initially selected by at least one server, and based at least in part on an initial presumptive cognitive diagnosis associated with the patient, in which objects associated with the first digital cognitive test are initially modified before being displayed based on physical attributes of the patient, and physical limitations of the patient, and wherein data indicating the initial presumptive cognitive diagnosis of the patient, the physical attributes of the patient, and the physical limitations of the patient, is accessible by the at least one server through one or more networks;
    receiving patient interactions with the first digital cognitive test on the touch screen computing device in response to the objects displayed with the first digital cognitive test;
    capturing, on the touch screen computing device, the patient interactions as first performance results corresponding to performance of the patient of first tasks of the first digital cognitive test;
    transmitting the first performance results to one or more database servers;
    determining, at the at least one server, one or more cognitive impairments of the patient based on the first performance results of the patient, and on metrics associated with the first performance results;
    mining, by the at least one database server, a stored second performance results of a previous patient;
    determining, by the at least one server, a first diagnostic accuracy of the first digital cognitive test in response to a comparing by the at least one server of the mined stored second performance results with the first performance results corresponding to performance of the patient of first tasks on the first digital cognitive test;
    wherein the determining further comprises:
        counting a number of times a first digital cognitive test is administered to a plurality of patients;
        comparing a plurality of results of the administration of the first digital cognitive test to the plurality of patients with at least one stored clinician diagnosis of a first cognitive impairment;
        associating an efficacy value with the first digital cognitive test and the first cognitive impairment; and
        storing the efficacy value by the database server in a database in association with the first digital cognitive test and the first cognitive impairment; and
    selecting, through the at least one server, a further digital cognitive test for displaying to the patient by the touch screen computing device, in response to the at least one efficacy value associated with the first digital cognitive test and the first cognitive impairment falling below a threshold.

2. The method of claim 1, further comprising:
    selecting, through the at least one server, when the first performance results fall below a threshold, a next digital cognitive test for displaying to the patient by the touch screen computing device to confirm the one or more cognitive impairments determined by the at least one server by further testing the cognitive functions associated with the first digital cognitive test, the next digital cognitive test being based on the one or more cognitive impairments determined by the at least one server, and being initially modified before being presented based on the physical attributes of the patient and the physical limitations of the patient;

administering to the patient the next digital cognitive test on the touch screen computing device, wherein the next digital cognitive test is presented on the touch screen computing device as a battery of one or more cognitive tests being selected through the at least one server, and based on at least one of: (a) the first performance results of the patient, and (b) performance results of other patients having one or more of: (i) substantially a same presumptive cognitive diagnosis as the patient; (ii) one or more substantially same physical attributes of the patient; and (iii) one or more substantially same physical limitations of the patient;

receiving patient interactions with the next digital cognitive test on the touch screen computing device;

capturing by the touch screen computing device performance results for the next digital cognitive test corresponding to performance of the patient of next tasks of the next digital cognitive test;

storing the performance results of the next digital cognitive test on one or more of the touch screen computing device and the at least one server;

transmitting the performance results of the next digital cognitive test to the one or more database servers; and based on the performance results of the next digital cognitive test, and on metrics associated with the performance results of the next digital cognitive test, when the performance results reach a threshold, selecting through the at least one server, at least one further digital cognitive test for displaying to the patient on the touch screen computing device, the at least one further digital cognitive test being a cognitive test useful to determine cognitive function of the patient.

3. The method of claim 1, wherein the first digital cognitive test comprises a language test presented in the user interface of the touch screen computing device, the language test comprising:

presenting a sequence of words each for a set time period;
waiting a delay period;
presenting the sequence of the words for the set time period or another time period; and
receiving text from the patient attempting to enter the sequence of the words.

4. The method of claim 1, wherein the first digital cognitive test comprises a finger tapping test operative to cause the touch screen computing device to measure a number of times the patient touches inside a displayed tap point during a specific timeframe.

5. The method of claim 1, wherein the first performance results comprise at least one member of a group comprising:

a count of a number of times the patient tapped inside a tap point during a specific timeframe;
a rhythm associated with touches of the patient; and
a spatial location of the touches of the patient in relation to the tap point.

6. The method of claim 1, wherein the first digital cognitive test comprises a trail test operative to cause the touch screen computing device to display a trail of points for the patient to trace from a beginning point to an ending point, and through intermediary points in a particular sequence according to indicators associated with the trail of points.

7. The method of claim 1, wherein the first digital cognitive test comprises a memory test operative to:

cause the touch screen computing device to display a sequence of images comprising previously shown images and distractors; and
instruct the patient to indicate which of the previously shown images were previously shown.

8. The method of claim 1, wherein the first digital cognitive test comprises an orientation test operative to cause the touch screen computing device to instruct the patient to select a current date and location from displayed date and location options displayed by the touch screen computing device.

9. The method of claim 1, wherein the first digital cognitive test comprises an attention/flexibility test operative to cause the touch screen computing device to present a sequence of text of one letter, number, or word at a time along with a plurality of descriptors of the presented text, and store patient selections of options for the sequence of text.

10. The method of claim 1, wherein the first digital cognitive test comprises a selected attention response test operative to cause the touch screen computing device to present a target, one or more distractors, and a plurality of interactive descriptors for describing the target.

11. The method of claim 1, wherein the first digital cognitive test comprises a visual spatial test to cause the touch screen computing device to present a sequence of text, and determine how fast and accurately the patient can tap through the sequence of text.

12. The method of claim 1, wherein the first digital cognitive test comprises a memory test to cause the touch screen computing device to present a sequence of text, instruct the patient to enter the sequence of text in a forward or backward manner, receive input text from the patient, and determine whether the input text received from the patient comprises the sequence of text in the instructed forward or backward manner.

13. The method of claim 1, wherein the at least one server is configured to:

provide at least the first digital cognitive test to a plurality of touch screen computing devices;
receive from the plurality of touch screen computing devices performance results of patients to whom the at least the first digital cognitive test was presented;
receive from the plurality of touch screen computing devices patient medical records associated with the patients, the patients having one or more of: (i) substantially a same presumptive cognitive diagnosis; (ii) one or more substantially same physical attributes; (iii) and one or more substantially same physical limitations; and
associate the performance results of the patients having at least a same presumptive cognitive diagnosis.

14. The method of claim 13, wherein the patient medical records comprise electronic indications corresponding to at least one member of a group comprising:

wallet-type information;
patient medical history;
familial medical history;
medications;
genetics;
diagnoses;
lab results; and
patient imaging.

15. The method of claim 13, wherein the one or more database servers are in bidirectional communication with the at least one server, the one or more database servers configured to:
- store the performance results associated with the patients to whom the at least the first digital cognitive test was presented;
- store the patient medical records associated with the patients to whom the at least the first digital cognitive test was presented; and
- transmit, upon request, one or more of: (i) a sample of the performance results, and (ii) a sample of the patient medical records.

16. A computer-implemented method for administering one or more cognitive tests for evaluating a patient for a cognitive impairment, the method implemented by a non-transitory computer readable storage medium storing one or more programs, the one or more programs comprising instructions, which, when executed by one or more servers having one or more processors, cause the at least one server to:
- generate a first battery of one or more cognitive tests for testing one or more cognitive functions of the patient, the first battery of one or more cognitive tests being based at least in part on an initial presumptive cognitive diagnosis associated with the patient, in which objects associated with the first battery of one or more cognitive tests are initially modified based on physical attributes of the patient and physical limitations of the patient, and wherein data indicating the initial presumptive cognitive diagnosis of the patient, and the physical attributes of the patient, and the physical limitations of the patient, are accessible by the at least one server through one or more networks;
- indicate to a client computing device having a user interface that the first battery of one or more cognitive tests is to be administered to the patient;
- receive from the client computing device patient performance results associated with patient interactions with the user interface of the client computing device obtained during the first battery of one or more cognitive tests, the patient performance results obtained after administration of the first battery of one or more tests to the patient;
- retrieve patient medical information about the patient, the patient medical information including the initial presumptive cognitive diagnosis of the patient, the physical attributes of the patient, and the physical limitations of the patient;
- analyze the performance results to determine one or more cognitive impairments of the patient;
- mine, by the at least one server, a stored second performance results of a previous patient;
- determining, by the at least one server, a first diagnostic accuracy of the first battery of one or more cognitive tests in response to a comparing by the at least one server of the mined stored performance results with the performance results corresponding to performance of the patient on the first battery of one or more cognitive tests:
  - wherein the determining further comprises:
    - counting a number of times the first battery of one or more cognitive tests is administered to a plurality of patients;
    - comparing a plurality of results of the administration of the first digital cognitive test to the plurality of patients with at least one stored clinician diagnosis of a first cognitive impairment;
    - associating an efficacy value with the first battery of one or more cognitive tests and the first cognitive impairment; and
    - storing the efficacy value by the server in a database in association with the first battery of one or more cognitive tests and the first cognitive impairment; and
- selecting, through the at least one server, a further battery of one or more cognitive tests for displaying to the patient by the touch screen computing device, in response to the at least one efficacy value associated with the first battery of one or more cognitive tests and the first cognitive impairment falling below a threshold; and
- transmit an indication to administer the further battery of one or more tests to the client computing device.

17. The method of claim 16, wherein the patient medical information comprises at least one member of a group comprising:
- wallet-type information;
- patient medical history;
- familial medical history;
- medications;
- genetics;
- diagnoses;
- lab results;
- patient imaging; and
- traumatic event details.

18. The method of claim 16, wherein the first battery and the second battery of one or more cognitive tests comprise at least one member of a group comprising:
- a finger tapping test;
- a trail test;
- an attention/flexibility test;
- a selective attention response test;
- a language test;
- a visual spatial test; and
- a memory test.

19. A system for administering one or more cognitive tests for evaluating a patient for a cognitive impairment, the system comprising:
- a touch screen computing device having a user interface configured to display a first digital cognitive test for testing one or more cognitive functions of the patient;
- a processor configured to select the first digital cognitive test and, based at least in part on an initial presumptive cognitive diagnosis associated with the patient, to modify objects associated with the first digital cognitive test before being displayed on the touch screen computing device, the modification being based on physical attributes of the patient, and physical limitations of the patient, and wherein data indicating the initial presumptive cognitive diagnosis of the patient, the physical attributes of the patient, and the physical limitations of the patient, is accessible by the processor,
- wherein the touch screen computing device is further configured to:
  - receive patient interactions with the first digital cognitive test in response to the objects displayed with the first digital cognitive test;
  - capture the patient interactions as first performance results corresponding to performance of the patient of first tasks of the first digital cognitive test; and
  - transmit the first performance results to one or more servers, wherein the server is further configured to:
mine, by the at least one server, a stored second performance results of a previous patient;
determine, by the at least one server, a first diagnostic accuracy of the first digital cognitive test in response to a comparing by the at least one server of the mined stored second performance results with the first performance results corresponding to performance of the patient of first tasks on the first digital cognitive test;
wherein the determining further comprises:
counting a number of times a first digital cognitive test is administered to a plurality of patients;
comparing a plurality of results of the administration of the first digital cognitive test to the plurality of patients with at least one stored clinician diagnosis of a first cognitive impairment;
associating an efficacy value with the first digital cognitive test and the first cognitive impairment; and
storing the efficacy value by the at least one server in a database in association with the first digital cognitive test and the first cognitive impairment; and
select, through the at least one server, a further digital cognitive test for displaying to the patient by the touch screen computing device, in response to the at least one efficacy value associated with the first digital cognitive test and the first cognitive impairment falling below a threshold;
analyze performance results of the patient performing the further digital cognitive test;
determine one or more cognitive impairments of the patient in response to the performance results of the patient performing the further digital cognitive test; and
select, when the performance results of the patient performing the further digital cognitive test fall below a threshold, a next digital cognitive test for displaying to the patient by the touch screen computing device to confirm the one or more cognitive impairments determined by the server by further testing the cognitive functions associated with the further digital cognitive test, the next digital cognitive test being based on the one or more cognitive impairments determined by the server, and being initially modified before being presented, the modification based on the physical attributes of the patient and the physical limitations of the patient.

* * * * *